United States Patent [19]

Cincotta

[11] Patent Number: 5,565,454
[45] Date of Patent: Oct. 15, 1996

[54] METHOD FOR PREVENTING INTERVENTION-ASSOCIATED STENOSIS AND OTHER SYMPTOMS ASSOCIATED WITH STENOSIS OF BLOOD VESSELS FOLLOWING NON-BYPASS, INVASIVE INTERVENTIONS

[75] Inventor: Anthony H. Cincotta, Andover, Mass.

[73] Assignee: Ergo Science, Incorporated, Charlestown, Mass.

[21] Appl. No.: 455,354

[22] Filed: May 31, 1995

[51] Int. Cl.⁶ .................. A61K 31/495; A61K 31/44; A61K 31/165
[52] U.S. Cl. .................. 514/250; 514/288; 514/619
[58] Field of Search .................. 514/250, 288, 514/619

[56] References Cited

U.S. PATENT DOCUMENTS

| | | | |
|---|---|---|---|
| 4,659,715 | 4/1987 | Meier et al. | 514/288 |
| 4,749,709 | 6/1988 | Meier et al. | 514/288 |
| 4,783,469 | 11/1988 | Meier et al. | 514/288 |
| 5,006,526 | 4/1991 | Meier et al. | 514/250 |
| 5,342,348 | 8/1994 | Kaplan | 604/891.1 |
| 5,344,832 | 9/1994 | Cincotta et al. | 514/288 |
| 5,468,755 | 11/1995 | Cincotta et al. | 514/288 |

*Primary Examiner*—Phyllis G. Spivack
*Attorney, Agent, or Firm*—Darby & Darby, P.C.

[57] ABSTRACT

The present invention relates to methods for reducing stenosis after non-bypass invasive intervention and for ameliorating symptomatic chest pains following non-bypass invasive intervention comprising administering a daily amount of a dopamine-potentiating/prolactin-reducing compound at a predetermined time and continuing administration for a period of time at least sufficient to permit the vascular injury to heal.

13 Claims, 1 Drawing Sheet

METHOD FOR PREVENTING INTERVENTION-ASSOCIATED STENOSIS AND OTHER SYMPTOMS ASSOCIATED WITH STENOSIS OF BLOOD VESSELS FOLLOWING NON-BYPASS, INVASIVE INTERVENTIONS

FIELD OF THE INVENTION

The invention relates to methods for reducing, in a subject animal (including a human) in need of such treatment, the rate at which blood vessels restenose after percutaneous transluminal coronary angioplasty (PTCA), atherectomy or endarterectomy. This invention also relates to methods for ameliorating symptomatic chest pain (angina pectoris or Amaurosis fugax) in humans that occurs after restenosis of a blood vessel following non-bypass invasive interventions, i.e. percutaneous transluminal corotary angioplasty, atherectomy and endarterectomy.

BACKGROUND OF THE INVENTION

Cardiovascular Disease and Non-Bypass Invasive Intervention

In the United States myocardial infarcts (MI) are a leading cause of death. Almost all myocardial infarcts are entirely attributable to atherosclerosis. Atherosclerosis is a slowly progressive disease that begins in childhood but does not become manifest until later in life when it results in clinical symptoms associated with damage to susceptible organs, primarily the heart and brain.

Atherosclerosis, often referred to as "hardening of the arteries", results from the formation on the internal arterial wall of lesions known as atheromas or fibrous plaques. The plaques are composed primarily of a core of lipid and cholesterol deposits surrounded by connective tissue and smooth muscle cells. Among the important risk factors for the development of atherosclerotic lesions are various metabolic disorders such as hyperlipidemia, hyperlipoproteinemia, diabetes, obesity, hyperglycemia and hyperinsulinemia. As the lesions increase in size, they can restrict the flow of blood in the artery leading to a variety of clinical outcomes. One such outcome is coronary ischemia which may clinically manifest itself as either angina pectoris (chest pain) or myocardial infarction. Another such outcome is cerebral ischemia which may lead to cerebral infarct (i.e., stroke) or ischemic encephalopathy.

Significant stenosis of coronary arteries can be treated by percutaneous transluminal coronary angioplasty (PTCA), also called balloon angioplasty, or by atherectomy. These treatments for coronary heart disease have become major alternatives to coronary bypass surgery. Similarly, stenoses of the internal carotid arteries, which cause cerebral ischemia and can lead to strokes, are removed by endarterectomy, a technique similar to atherectomy.

In the United States, alone, approximately 400,000 people undergo PTCA each year. Unfortunately, 25–50% of those patients treated by PTCA experience recurrent ischemia, within six months, as a result of restenosis of the arteries.

Restenosis is, in part, due to the injury of the arterial endothelium that occurs during angioplasty. This injury results in a focal increase in permeability to plasma constituents and allows platelets and monocytes to adhere to the endothelium or subendothelial connective tissue. Activated platelets and monocytes will secrete a variety of potent cytokines (eg. platelet derived growth factor (PDGF), epidermal growth factor (EGF), fibroblast growth factor (FGF), interleukin- 1 (IL-1) and tumor necrosis factor (TNF)) that result in recruitment of fibroblasts and smooth muscle cells into the area and in hyperproliferation of the smooth muscle cells. The smooth muscle cells synthesize extracellular matrix components such as collagen, elastic fibers and proteoglycans. Monocytes also migrate into the intima of the blood vessels and transform into foam cells, which are activated macrophages that actively accumulate lipids and store them as intracellular lipid droplets. Hyperlipidemia also appears to have a role, though as yet poorly defined, in the generation of post-treatment lesions. Restenosis results in recurrence of ischemia and its symptoms including angina, abnormal electrocardiogram readings, and can result in myocardial infarction.

Researchers have tried to prevent restenosis with a variety of pharmacological, biotechnological and mechanical approaches. To date, despite substantial efforts, no strategy has yet been developed that significantly reduces the restenosis rate. In fact, in recent years, over 50 drugs have been used in attempts to prevent restenosis without success.

Previous Work of the Present Inventors

The present inventors and their co-workers have found that administration of certain dopamine potentiating and/or prolactin reducing compounds (e.g., dopamine agonists such as bromocriptine) and/or prolactin enhancers (e.g., dopamine antagonists, such as metoclopramide; serotonin agonists and precursors, such as 5-hydroxytryptophan) and particularly administration of such substances at predetermined times, reduce body fat stores, obesity, plasma triglycerides and cholesterol and can prevent or alleviate atherosclerosis as well as hyperinsulinemia and insulin resistance. (See U.S. Pat. Nos. 4,659,715; 4,749,709; 4,783,469; 5,006,526; 5,344,832; and PCT U.S. application Ser. No. 92/11166.

Related Applications

Co-pending patent application Ser. No. 07/919,685 discloses methods for regulating lipid metabolism disorders by administering prolactin (or both prolactin and a glucocorticosteroid ("GC")) into the bloodstream of an animal or human on a timed daily basis in an amount and for a period of time sufficient to modify and reset the neural phase oscillation of the prolactin daily rhythm. This modification was found to increase insulin sensitivity. The prolactin injections are timed to create a peak in the subject's daily prolactin (or both prolactin and glucocorticosteroid) secretion profile that coincides in time with the peak prolactin secretion (or prolactin and GC peaks, respectively) of a lean, insulin-sensitive human in order to increase insulin sensitivity and reduce body fat stores.

Ser. No. 07/719,745 also discloses and claims the further administration of a thyroid hormone to subjects that are being treated with a domamine agonist and prolactin enhancer, especially to those subjects that are chronically or seasonally hypothyroid.

Co-pending applications Ser. Nos. 07/995,292 and 08/264,558 disclose methods for determining whether the daily circulating prolactin profile in a subject is abnormal, and methods for normalizing prolactin profiles found to be aberrant. In pertinent part, the treatment method involves administration of a prolactin reducing compound no later than the time at which during waking hours prolactin level in the subject to be treated is at its highest, and may also involve administration of a prolactin enhancer timed to cause a peak of prolactin level to occur during night-time. The objective of this treatment is alteration ("sculpting") of the subject's prolactin profile to mimic or approach in phase and amplitude the profile of a lean healthy human not suffering from any disorders.

Co-pending patent application Ser. No.08/263,607 discloses methods for regulating lipid and glucose metabolism by the timed administration of pirenzepine, methyl scopolamine or another muscarinic (preferably M1), receptor antagonist alone or in combination with a prolactin reducing compound as a treatment for diabetes. This application further discloses maintaining therapy for a sufficient period of time to cause a resetting of neural phase oscillators controlling the prolactin daily rhythm resulting in the continuing metabolic improvement after the cessation of therapy.

Co-pending patent application Ser. No.08/271,881 discloses a method of adjusting the phase relationship between the circadian rhythms for prolactin and for one or more immune responses. The invention involves normalizing (or resetting) the circadian rhythm for prolactin to resemble that of a healthy young subject. The invention also involves manipulating the circadian rhythm for prolactin to bring it in such a phase and amplitude relation with the immunologic responsiveness to prolactin as to exert an amplifying effect on a predetermined aspect of the immune response.

OBJECTS OF THE INVENTION

It is an object of this invention to provide methods for totally or partially preventing restenosis and/or eliminating one or more clinical symptoms associated with restenosis, such as chest pain, thereby extending the benefit of PTCA, arthrectomy and/or endarterectomy.

In particular, it is an object of this invention to provide a pharmacological method for the treatment of mammals, including humans, that typically develop recurrent coronary ischemia within six months of undergoing percutaneous transluminal coronary angioplasty or atherectomy.

Another object of this invention is to provide a pharmacological method for the treatment of mammals, including humans, that develop recurrent cerebral ischemia within six months of undergoing endarterectomy.

A more specific object of the invention is to provide a pharmacological method of reducing or preventing chest pain or Amaurosis fugax that may occur in a mammal in need of such treatment.

Another more specific object of the invention is to provide a pharmacological method of reducing or preventing restenosis of arteries which have undergone compression or removal of atherosclerotic lesions.

SUMMARY OF THE INVENTION

Disclosed is a method for preventing or limiting restenosis in a mammal (including humans) having undergone a non-bypass invasive procedure selected from the group consisting of (i) percutaneous transluminal coronary angioplasty; (ii) atherectomy; and (iii) endarterectomy. The method comprises administering to the mammal a daily amount of a dopamine-potentiating/prolactin-reducing compound at a predetermined time, the time and amount being selected to reduce the blood prolactin level and/or increase dopamine activity in the subject during all or a portion of the daytime hours 0700–2200; and continuing the administration for a period of time at least sufficient to permit vascular injury incident to the invasive procedure to heal.

Also disclosed is a method for reducing or eliminating chest pain in a human having undergone a non-bypass invasive procedure selected from the group consisting of (i) percutaneous transluminal coronary angioplasty; (ii) atherectomy; and (iii) endarterectomy. The method comprises administering to a human a daily amount of a dopamine-potentiating/prolactin-reducing compound at a predetermined time, the time and amount being selected to reduce the blood prolactin level and/or increase dopamine activity in the subject during all or a portion of the daytime hours 0700–2200; and continuing the administration for a period of time at least sufficient to permit vascular injury incident to the invasive procedure to heal.

DETAILED DESCRIPTION OF THE INVENTION

Figure 1:
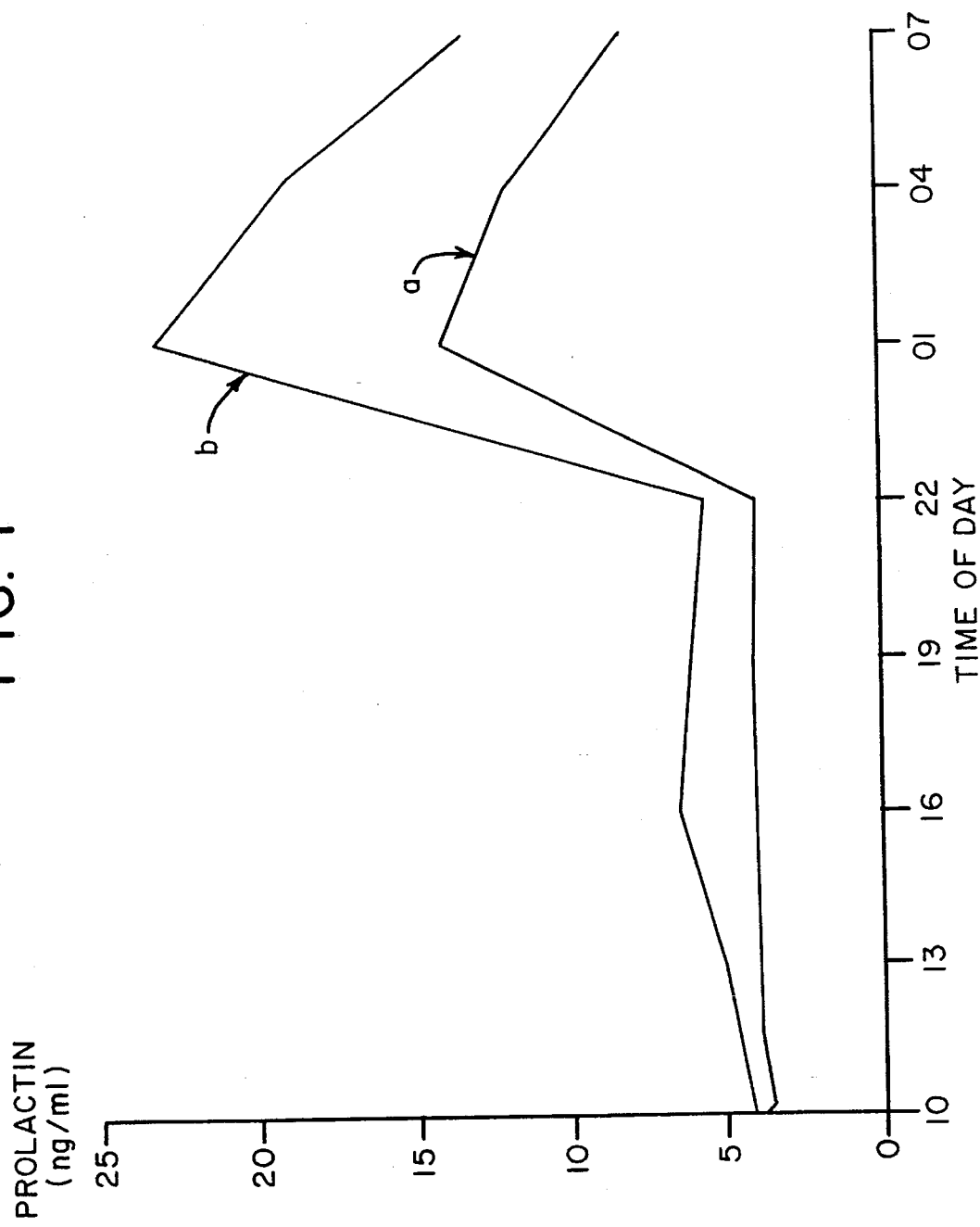
FIG. 1 depicts the normal or healthy prolactin profiles for humans. Curve "a" depicts the profile of healthy males and curve "b" depicts the profile of healthy females.

All patents, patent applications and literature references cited herein are incorporated by reference in their entirety as if their disclosures were physically present in the present specification. In case of conflict, however, the present disclosure controls.

It has recently been discovered that the restenosis of blood vessels after non-bypass, invasive intervention can be partially or totally abrogated by administering to a mammalian subject (including a human) a dopamine-potentiating/prolactin-reducing compound daily at a predetermined time during a 24-hour period designed to decrease the blood prolactin level and/or increase dopamine activity of said subject during at least a substantial portion of the daytime (07:00–22:00). This administration also serves to partially or totally abrogate chest pain typically suffered by humans as a result of the restenosis of blood vessels subsequent to non-bypass invasive procedures. Non-bypass invasive intervention in blood vessels (arteries) such as PTCA, atherectomy, or endarterectomy is a mechanical ablation or removal of arterial plaques. Typically, the subjects undergoing such procedures suffer from metabolic abnormalities.

Healthy (normal) subjects, i.e., lean young members of a species not suffering from metabolic abnormalities, have highly predictable daily prolactin release profiles, which in humans are characterized by a low and relatively constant prolactin level during the waking hours (daytime: 07:00–22:00) followed by a sharp rise to a peak during night-time and subsequent more gradual tapering down to the waking hours level by morning (22:00–07:00). FIG. 1 depicts the normal or healthy prolactin profile for humans (curve a: males; curve b: females).

Subjects suffering from metabolic abnormalities have abnormal circadian rhythms of plasma prolactin. The majority of these abnormal profiles include abnormally high prolactin levels during daytime. Abnormally high daytime levels are those higher than the normal level by at least 1 SEM above the corresponding point of the normal profile, if a complete profile has been generated for the subject, and by at least 2 SEM, if only 3 or 4 key prolactin levels have been measured. 1 SEM is 1–2 ng/ml for males and 1–3 ng/ml for females during waking hours.

Instead of (or in addition to) abnormally high daytime prolactin levels, some subjects with metabolic abnormalities exhibit abnormally low night-time prolactin levels, i.e., levels at least 1 SEM below the corresponding levels of healthy subjects if a complete prolactin profile has been generated and at least 2 SEM below the corresponding healthy levels if only one or two key night-time prolactin level(s) has (have) been measured. In human males, 1 SEM for night-time prolactin levels is about 3 ng/ml; in human females, 1 SEM for night-time prolactin levels is between about 3 and 6 ng/ml.

A prolactin profile of a subject is obtained by collecting blood samples from the subject at a plurality of time points during a 24-hour time period (preferably at 3 hour intervals), assaying each blood sample for prolactin content, plotting the time of blood sampling against the quantity of prolactin present in each sample to generate a data point for each sample, and connecting the data points (or fitting a curve through them) to form the subject's prolactin profile. Generation of prolactin profiles has been described in detail in related applications Ser. Nos. 07/995,292 and 08/264,558.

A baseline prolactin profile is generated, preferably, before the invasive intervention. If this is not possible, a prolactin profile should be generated as soon after the intervention as practical, within 30 days, preferably within 10 days of the procedure.

To prevent possible restenosis or chest pain in a subject who has undergone non-bypass invasive intervention, a dopamine potentiating/prolactin reducing compound (e.g., bromocriptine) is administered following such intervention. Therapy may, in fact, begin prior to the intervention if desired. Therapy, in the latter case, may begin as early as the diagnosis leading to the intervention.

"Prolactin reducing compound" shall include substances which directly or indirectly inhibit prolactin secretion or accelerate prolactin depletion in a subject (mammals including humans). Additionally, these compounds can increase dopamine activity. Non-limiting examples of prolactin reducing compounds include dopamine potentiating compounds, dopamine agonists (particularly d2 dopamine agonists) such as dopamine and certain ergot-related prolactin-inhibiting compounds.

Non-limiting examples of d2 dopamine agonists are 2-bromo-alpha-ergocriptine; 6-methyl-8-beta-carbobenzy-loxy-aminoethyl- 10-alpha-ergoline; 8-acylaminoergolines, 6-methyl-8-alpha-(N-acyl)amino- 9-ergoline; 6-methyl-8-alpha-(N-phenyl-acetyl)amino- 9-ergoline; ergocornine; 9,10-dihydroergocornine; and D-2-halo-6-alkyl-8-substituted ergolines, e.g., D-2-bromo-6-methyl- 8-cyanomethyl-ergoline. Moreover, the non-toxic salts of the prolactin-inhibiting ergot-related compounds formed from pharmaceutically acceptable acids are also useful in the practice of this invention. Bromocriptine, or 2-bromo-alpha-ergocryptine, has been found particularly useful in the practice of this invention.

If the subject who has undergone non-bypass invasive intervention has abnormally low night-time prolactin levels, a prolactin enhancer (i.e., a compound that increases circulating prolactin levels) is administered. This therapy can be used on its own or as an adjunct to administration of a prolactin reducing compound if such combination is warranted, (i.e., if the subject as diagnosed has both abnormally high daytime prolactin levels and abnormally low night-time prolactin levels or if the subject's treatment with a dopamine potentiating/prolactin reducing compound to decrease his/her daytime prolactin levels causes a decrease also in the night-time prolactin levels). Again, therapy should begin immediately following the intervention, but may begin as early as the diagnosis which leads to the non-bypass invasive intervention.

"Prolactin enhancer" shall include substances which directly or indirectly stimulate prolactin secretion or inhibit prolactin elimination. Non-limiting examples of a prolactin enhancer include prolactin; melatonin; dopamine antagonists such as metoclopramide, haloperidol, pimozide, phenothiazine, domperidone, sulpiride and chlorpromazine; serotonin agonists (i.e., MAO inhibitors), e.g., pargyline, synthetic morphine analogs, methadone; antiemetics, e.g., metoclopramide; estrogens; and various other serotonin agonists, e.g., tryptophan, 5-hydroxytryptophan (5-HTP), fluoxirane, and dexfenfluramine. Moreover, the non-toxic salts of the foregoing prolactin enhancing compounds formed from pharmaceutically acceptable acids are also useful in the practice of this invention. Metoclopramide has been found particularly useful in the practice of this invention.

"Prolactin modulator" shall refer to either prolactin enhancers, prolactin reducers, or both.

In treating mammals, generally, dosages of the dopamine potentiating/prolactin reducing compound (e.g., bromocriptine) and/or enhancer (e.g., metoclopramide), respectively, are each given generally once a day. Therapy should last at least until the tissue injured by the intervention heals, generally 6 to 24 months. The preferred dopamine potentiating/prolactin reducing compound (bromocriptine) is given daily at dosage levels ranging from about 3 micrograms to about 200 micrograms, preferably from about 10 micrograms to about 100 micrograms, per kg. of body weight, and the prolactin enhancer (e.g., metoclopramide) is given daily at dosage levels ranging from about 5 micrograms to about 100 micrograms, preferably from about 10 micrograms to about 50 micrograms, per kg. of body weight per day to modify, or alter, the prolactin secretion profile and continued for a time sufficient to reset the circadian plasma prolactin rhythm.

In treating humans, the dopamine potentiating/prolactin reducing compound (e.g. bromocriptine) is generally given at daily dosage levels ranging from about 3 micrograms to about 200 micrograms, preferably from about 10 micrograms to about 100 micrograms, per kg. of body weight. The prolactin enhancer metoclopramide is generally given at daily dosage levels ranging from about 5 micrograms to about 100 micrograms, preferably from about 10 micrograms to about 50 micrograms, per kg. of body weight per day.

Such treatment (using one or both types of drugs) is typically continued over a period of time ranging from about 10 days to usually about 180 days, but may be continued for longer periods such as several years.

In the practice of this invention, a dopamine potentiating/prolactin reducing compound, and/or a prolactin enhancer are administered daily to a subject preferably orally, or by subcutaneous, intravenous or intramuscular injection. Each prolactin modulator is administered in one or multiple dosages at a predetermined time or at more than one predetermined time or times to reduce daytime prolactin levels. The amount(s) and time(s) of prolactin modulator administration may be adjusted if needed based on subsequently measured prolactin profile (or levels) of the patient and the criteria and guidelines described in Ser. No. 08/264, 558. For example, if the prolactin enhancer causes prolactin levels to stay high into the daytime, the amount or the time of administration or both will be adjusted to avoid this. The objective is to reduce abnormally daytime high prolactin levels and/or to increase abnormally low night-time levels to mimic or approach the corresponding normal levels. Assessment of the effectiveness of the treatment can be made by subtracting a "key" prolactin level of the subject from the corresponding normal level (or vice versa) and determining whether the difference exceeds two standard errors of the mean. If a complete prolactin profile is generated, this assessment can be made by subtracting the difference between any point on the patient's profile from the corresponding point on the normal prolactin curve and determining whether the difference exceeds on SEM; alternatively, the assessment can be made by comparing the difference in the area under the curve between the patient's profile and the normal profile.

Additional prolactin profiles or key levels are measured periodically during therapy to assess the efficacy of the administered modulator(s) in adjusting prolactin levels. Preferably, such measurements are taken or such profile is generated every 4 weeks during the first 3 months of therapy, and then every 24 weeks thereafter.

The following examples illustrate the present invention without limiting its scope:

EXAMPLE 1

Direct Effect of Bromocriptine on Smooth Muscle Cell Proliferation

An in vitro preparation of rat smooth muscle cells ($5 \times 10^3$) was cultured in DMEM plus fetal calf serum (2%), and either prolactin, PDGF, or prolactin plus PDGF. Each of these media preparations was incubated with or without bromocriptine.

Bromocriptine ($10^{-7}$ to $10^{-5}$M) was added to each culture and the cells were incubated at 37° C. for 24 hours. Proliferation of smooth muscle cells was assessed by $^3$H-thymidine incorporation and compared to controls (to which no bromocriptine was added).

The results were as follows:

Bromocriptine at a dose of $10^{-7}$M inhibited fetal calf serum stimulated smooth muscle cell proliferation and at a dose of $10^{-5}$M inhibited prolactin, PDGF, and prolactin plus PDGF stimulated smooth muscle cell proliferation by 30–50%.

This experiment demonstrates that bromocriptine has a direct inhibitory effect on arterial wall smooth muscle cell proliferation. Although not to be bound by theory, the inventors believe that bromocriptine works at a cellular level (i.e., directly on the smooth muscle cells) by blocking $Ca^{++}$ influx and inhibiting Protein Kinase C activity, possibly, in part, by binding to $D_2$ receptors on the cell surface. This direct effect is in addition to and independent of the ability of bromocriptine to decrease prolactin levels, and is believed to be a contributing factor to the ability of bromocriptine to prevent restenosis.

EXAMPLE 2

Human Case Study of Restenosis Prevention and Chest Pain Abrogation

Patent SC (42 years, 180 lbs.) suffered an acute inferior myocardial infarction diagnosed based on symptoms and electro-cardiogram. He was treated with TPA and, eight days later, an angiogram was conducted which showed moderate to severe atherosclerosis with 99% stenosis in the left circumflex artery and 50% stenosis in the left coronary artery.

Two days thereafter PTCA was performed which reopened the lumen of the circumflex artery to about 80% of the original cross-sectional area of the circumflex artery (i.e., 20% post-PTCA stenosis), as determined by angiography.

One week after the post-PTCA angiography, a thallium stress test was performed which confirmed blood flow to the damaged area but resulted in ECG abnormalities about 9 minutes into the test. The abnormalities were associated with the damaged heart area distal to the infarct.

Plasma lipid analysis showed elevated triglyceride (about 400 ng/dl) and total cholesterol (about 250 ng/dl) levels. The subject was medicated with Cardizam 30 mg/day, Mevacor (40 mg/day) and aspirin (325 mg/day).

Six weeks following the initiation of medication there were no significant changes to triglyceride and cholesterol levels but the subject began experiencing chest pain induced by mild exercise (½ mile walk). Chest pain increased in the following two weeks and because of this exercise was discontinued. Cold weather also induced severe chest pain. The subject was then administered bromocriptine (1.25 mg/day at 08:00) and metoclopramide (5 mg/day at 23:00) after a prolactin profile demonstrated elevated prolactin levels during the period 08:00–21:00 hours.

The chest pain quickly subsided after the initiation of prolactin modulation therapy. Bromocriptine dose was increased to 2.5 mg/day after 4 weeks. After an additional six months, total cholesterol was reduced by 60% and triglycerides were unaltered. Daytime prolactin levels were also reduced by 50%. A thallium stress test and ECG performed at this time showed no decrease in blood flow compared with the ECG following PTCA and the time period before ECG abnormalities were apparent slightly increased (from 9 to 11.5 minutes). Chest pain was not experienced during the stress test at all. Cold weather-induced chest pain also disappeared. The subject has continued on the prolactin modulator therapy for 2.5 years with no changes in his condition.

This case study indicates that prolactin modulators have a beneficial effect in reducing or eliminating chest pain and in preventing restenosis.

What is claimed is:

1. A method for preventing or limiting restenosis in a mammal having undergone a non-bypass invasive procedure selected from the group consisting of (i) percutaneous transluminal coronary angioplasty; (ii) atherectomy; and (iii) endarterectomy, which comprises:

(a) orally or parenterally administering to said mammal a daily amount of a dopamine-potentiating/prolactin-reducing compound at a first predetermined time said time being selected to reduce the blood prolactin level of said subject during all or a portion of the daytime hours 07:00–22:00; and (b) continuing said administration for a period of time at least sufficient to permit vascular injury incident to said invasive procedure to heal.

2. The method of claim 1 wherein said administration continues for a period in excess of about one year.

3. The method of claim 1 wherein said dopamine-potentiating/prolactin-reducing compound is administered as a single dosage.

4. The method of claim 1 wherein said dopamine-potentiating/prolactin-reducing compound is administered as multiple dosages.

5. The method of claim 1 wherein said dopamine-potentiating/prolactin-reducing compound is bromocriptine.

6. The method of claim 5 wherein said daily amount of bromocriptine is in a range of about 0.8 to 8.0 mg.

7. The method of claim 1 wherein said dopamine-potentiating/prolactin-reducing compound is bromocriptine and said daily amount is about 0.2 to 15 mg.

8. The method of claim 1 wherein an additional step of orally or parenterally administering a daily amount of a prolactin-enhancing compound at a second predetermined time to elevate the night-time prolactin level is performed.

9. The method of claim 8 wherein said prolactin-enhancing compound is metoclopramide.

10. The method of claim 9 wherein said daily amount of metoclopramide is in the range of about 0.5 to 2.0 mg.

11. The method of claim 8 wherein said prolactin-enhancing compound is metoclopramide and said daily amount is about 0.5 to 5.0 mg.

12. The method of claim 1 wherein said non-bypass invasive procedure is percutaneous transluminal coronary angioplasty.

13. A method for reducing or eliminating angina pectoris or amaurosis fugax in a mammal having undergone a non-bypass invasive procedure selected from the group consisting of (i) percutaneous transluminal coronary angioplasty; (ii) atherectomy; and (iii) endarterectomy, which comprises:

(a) orally or parenterally administering to said mammal a daily amount of a dopamine-potentiating/prolactin-reducing compound at a predetermined time said time being selected to reduce the blood prolactin level of said subject during all or a portion of the daytime hours 07:00–22:00; and (b) continuing said administration for a period of time at least sufficient to permit vascular injury incident to said invasive procedure to heal.

* * * * *